United States Patent [19]

Paulsen

[11] Patent Number: 5,284,845
[45] Date of Patent: Feb. 8, 1994

[54] USE OF ORAL DIAZOXIDE FOR THE TREATMENT OF DISORDERS IN GLUCOSE METABOLISM

[76] Inventor: Elsa P. Paulsen, 1115 Hilltop Rd., Charlottesville, Va. 22903

[21] Appl. No.: 936,867

[22] Filed: Aug. 27, 1992

Related U.S. Application Data

[63] Continuation of Ser. No. 669,386, Mar. 14, 1991, abandoned.

[51] Int. Cl.$^5$ .............................................. A61K 31/54
[52] U.S. Cl. .................................... 514/223.2; 424/9; 514/866
[58] Field of Search .............................. 514/223.2, 866

[56] References Cited

PUBLICATIONS

Chemical Abstracts 69:75522e (1968).
Chemical Abstracts 95:74402n (1981).
Arteriosclerosis, vol. 5, No. 4, Jul./Aug. 1985: *Impaired Glucose Tolerance*, Peter H. Bennett, National Institute of Arthritis, Diabetes, and Digestive and Kidney Diseases, Phoeniz, Ariz, pp. 315-317.
J. Chron. Dis., vol. 37, No. 8, pp. 667-669, 1984, Pergamon Press Ltd., UK: *Some Thoughts on Early Detection and Intervention in Diabetes Mellitus*, Victor M. Hawthorne and Catherine C. Cowie, University of Michigan, Ann Arbor, Mich.
Diabetic Medicine, 1991, John Wiley & Sons, Ltd.: *Reactive Hypoglycaemia in Association with Disordered Islet Function and Abnormal Hepatic Glucose-6-Phosphatase Activity: Response to Diazoxide*, J. Pears et al., Ninewells Hospital Medical School. Dundee, Scotland, pp. 268-271.
Diabetes, vol. 5, No. 67, Nov./Dec. 1956; *Spontaneous Hypoglycemia as an Early Manifestation of Diabetes Mellitus*, Holbrooke S. Seltzer et al., Ann Arbor, Mich, pp. 437-440.
Diabetes Care, vol. 13, No. 5, May 1990; Stuart A. Chalew et al.: *Evidence for Elevated Glucose Threshold in Patients With Impaired Glucose Tolerance and Symptoms of Hypoglycemia During OGTT.*
New England Journal Of Medicine, vol. 318, No. 19, May 12, 1988: Impaired Glucose Tolerance as a Disorder of Insulin Action, Stephen Lillioja et al.
Diabetes, vol. 36, Apr. 1987: *Prevalence of Diabetes and Impaired Glucose Tolerance and Plasma Glucose Levels in U.S. Population Aged 20-74 Yr*, Maureen I. Harris et al., pp. 523-534.
Diabetes Care, vol. 12, No. 7, Jul./Aug. 1989: *Impaired Gluocse Tolerance in the U.S. Population* Maureen I. Harris, pp. 464-474.
Horm. Metabol. Res. 18 (1986) 38-41, George Thieme Verlag Stutgart, New York, N.Y.: *Post-Receptor Insulin Resistance after Diazoxide in Non-Insulin Dependent Diabetes*, S. A. Olczak et al., pp. 38-41.
Long-term treatment with diazoxide in childhood hyperinsulinism, D. B. Grant et al. (1987).
Journal of Pediatrics, Jun. 1991, vol. 118, No. 6, pp. 906-909: *Hypertrophic cardiomyopathy after prolonged diazoxide therapy for hyperinsulinemic hypoglycemia*, Janis J. Parker et al.

(List continued on next page.)

*Primary Examiner*—Leonard Schenkman
*Attorney, Agent, or Firm*—Kenyon & Kenyon

[57] ABSTRACT

A method is disclosed for normalizing blood glucose and insulin levels as measured by an oral glucose tolerance test in an individual exhibiting normal fasting blood glucose and insulin levels and exhibiting in an oral glucose tolerance test elevated glucose levels and at least one insulin level abnormality selected from the group consisting of a delayed insulin peak, an exaggerated insulin peak and a secondary elevated insulin peak. The method comprises administering diazoxide to the individual before ingestion of a food source in an amount effective to normalize the blood glucose and insulin levels. Diazoxide is administered in an amount from about 0.4 to about 0.8 mg/kg body weight before each meal.

9 Claims, 5 Drawing Sheets

OTHER PUBLICATIONS

Williams Textbook Of Endocrinology, W. B. Saunders Company, Philadelphia, Pa.: *Long-Term Treatment*, p. 1247, Philip E. Cryer (1992).

International Journal Of Obesity (1983) 7, 453-458: *Effect of Pharmacological Suppression of Insulin Secretion on Tissue Sensitivity to Insulin in Subjects with Moderate Obesity*, Klaus Peter Ratzmann et al.

Henquin, et al., *Diabetes* 31: 776-783 (1982).

Eriksson, et al., *NEJM* 321(6): 337-343 (1989).

Saad, et al., The Lancet Jun. 17, 1989: 1356-1359.

Olefsky, J. M. in *Endocrinology*, DeGroot et al. (eds) Chapter 82 (1989).

Foster, D. W. *Diabetes Mellitus* in The Metabolic Basis of Inherited Disease 5th Ed. Stanbury et al. (eds) (1983).

Goodman and Gilman's *The Pharmacological Basis of Therapeutics* Chapter 64: Insulin and oral Hypoglycemic Drugs (1985).

USE OF ORAL DIAZOXIDE FOR THE TREATMENT OF DISORDERS IN GLUCOSE METABOLISM

This application is a continuation of U.S. application Ser. No. 07/669,386, filed on Mar. 14, 1991, now abandoned.

This invention relates to the utilization of oral diazoxide for the treatment of disorders caused by defects in glucose metabolism, including hyperglycemia and hypoglycemia. This invention also relates to use of diazoxide to delay or prevent onset of insulin dependency in Type II diabetic subjects. The responsiveness of patients to diazoxide treatment may also provide a useful tool for diagnosing Type II or pre-Type II diabetes.

BACKGROUND OF THE INVENTION

The central role of insulin in human metabolism is to aid in the transport of glucose into muscle and fat cells. The disease states, such as diabetes mellitus, which result from defects in either the ability of the body to produce insulin or in defective insulin binding are well documented.

Type I or insulin dependent diabetes is characterized by decreased insulin production leading to hyperglycemia, ketoacidosis, thirst and weight loss. In general, defects in insulin production or activity are associated with hyperglycemia, i.e. the failure of cells to take up glucose and subsequent high circulating blood levels.

Epidemiological studies indicate that Type I diabetes, or non-insulin-dependent diabetes mellitus (NIDDM) can be characterized by high, normal or low insulin concentrations and insulin response to glucose. The Lancet, Jun. 17, 1989; p. 1356-1359. In general, NIDDM is associated with either insulin resistance or defective insulin secretion.

Recent studies have indicated a high correlation between defective glucose metabolism and relatives with NIDDM. Estimates are that 43 percent of first degree relatives of patients with NIDDM develop the disease. Raised fasting and glucose-stimulated insulin concentrations are early abnormalities in subjects destined to develop NIDDM. Even individuals with a family history of NIDDM who have normal blood glucose concentrations have higher insulin concentrations than individuals without a family history of NIDDM, indicating an increased insulin resistance despite the apparent lack of a disease state. Nagulesparan M. et. al. Diabetes (1979) 28: 980-83; Hollenbeck et. al. Diabetes (1984) 33:460-463; Lilloja et. al. Diabetes (1987) 36:1329-1335.

Many patients that show early signs of defective glucose metabolism experience disorders such a lack of concentration, depression and abnormal weight gain. Eriksson et. al. NEJM (1989) 321(6): 337-343. Apparently, the glucose receptor in the beta cell does not respond promptly, giving either a poor or delayed insulin response; and the insulin receptor in the muscle cell is slow to act and therefore the glucose does not get into the cell promptly. The result is hyperglycemia of varying intensity. Continued stimulation of the beta cell occurs, with gradually rising blood insulin levels until finally the insulin receptors respond, the blood glucose rushes into the cells and hypoglycemia results. Such hypoglycemia is generally referred to as reactive hypoglycemia.

Because this sequence of events occurs within 3 to 4 hours of a meal, the ensuing hypoglycemia remains undetected when a standard two hour test such as a glucose tolerance test, a two-hour euglycemic, hyperinsulinemic clamp and a hyperglycemicglucose clamp are utilized to measure glucose tolerance. Accordingly, the hyperglycemic state may be observed, while the following hypoglycemic reaction is not. Such studies indicate that relatives of patients with NIDDM had the same degree of disturbed glucose metabolism as patients diagnosed with the disease, creating a hyperglycemic state regardless of the relatively normal or high levels of circulating insulin. In each case, the level of glucose after two hours is higher than normal.

Oral diazoxide (7-chloro-3-methyl-2H-1,2,4-benzothiadiazine 1,1-diazoxide) is a drug originally developed for the treatment of hypertension. It is now used primarily for the treatment of hypoglycemia due to hyperinsulinism, associated with conditions such as inoperable islet cell adenoma or carcinoma. It is also used to suppress insulin in cases of nesidioblastosis in infants or, at times, in adenomas pre-operatively. It is currently marketed by prescription in the U.S. under the tradename Proglycem ®.

Diazoxide is known to cause hyperglycemia which is usually transitory (maximum 8 hours) and is due to decreased insulin secretion and decreased peripheral utilization of glucose. Henquin et. al. Diabetes 31:766-783 (1982).

Despite the extensive amount of research dedicated to understanding glucose metabolism and the defects that result from defects in such metabolism, many persons suffer from hyperglycemic and hypoglycemic symptoms that remain undiagnosed. Of such undiagnosed illnesses, reactive hypoglycemia is a debilitating disease that often causes severe psychological problems.

It is the object of the present invention to provide a method of diagnosing and treating reactive hypoglycemia.

It is a further object of the invention to enhance the release of insulin and/or uptake of sugar in persons with disorders in glucose metabolism through the use of oral diazoxide.

It is a further object of the invention to provide a means of diagnosing Type II or pre-Type II diabetic conditions.

It is a further object of the invention to prevent or delay the onset of insulin dependency in patients having pre-or early Type II diabetes.

It is a further object of the invention to provide a method of treating obesity caused by defective glucose metabolism through the use of oral diazoxide.

These as well as other objects of this invention are realized in light of the following disclosure.

SUMMARY OF THE INVENTION

Oral diazoxide is used to normalize the insulin secretion and glucose utilization in patients suffering from hyperglycemia, followed by reactive hypoglycemia. The lowering of both glucose and insulin levels and eventual normalizing of the timing of their peak levels achieved when the drug is orally administered prior to each meal, strongly suggests that the diazoxide is enhancing activity of the glucose receptor on the beta cell and the insulin receptor on the peripheral muscle cell. Insulin is promptly released, and peripheral glucose utilization in the muscle cells is normalized.

A method is disclosed for normalizing blood glucose and insulin levels as measured by an oral glucose tolerance test in an individual exhibiting normal fasting blood glucose and insulin levels and exhibiting in an oral glucose tolerance test elevated glucose levels and at least one insulin level abnormality selected from the group consisting of a delayed insulin peak, an exaggerated insulin peak and a secondary elevated insulin peak. The method comprises administering diazoxide to the individual before ingestion of a food source in an amount effective to normalize the blood glucose and insulin levels. Diazoxide is administered in an amount from about 0.4 to about 0.8 mg/kg body weight before each meal.

DETAILED DESCRIPTION OF THE INVENTION

Figure 1A:
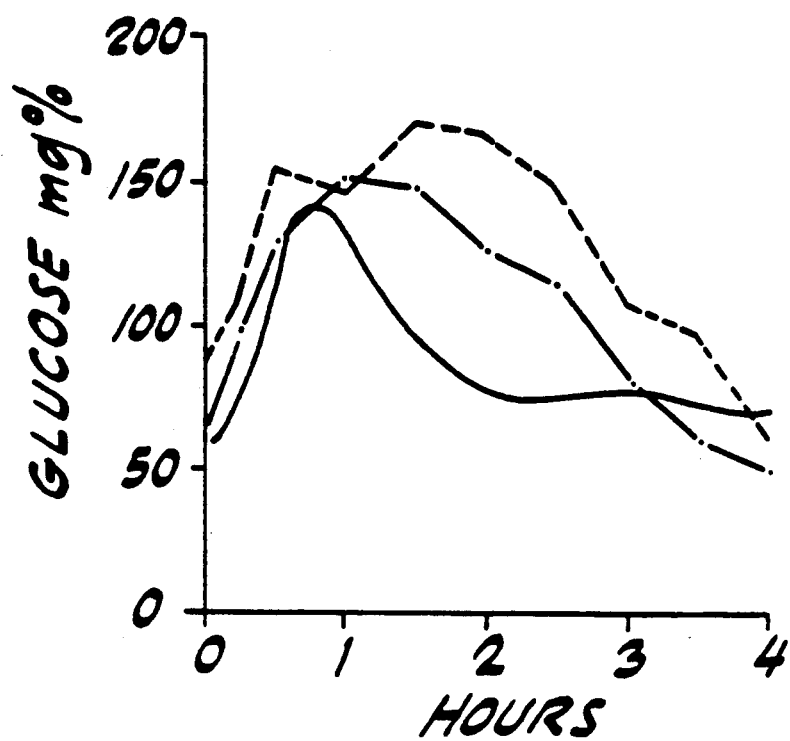
FIG. 1A and 1B demonstrate the effect of a single dose of oral diazoxide on glucose and insulin levels.

The standard test for diagnosing defects in glucose metabolism is the oral glucose tolerance test (OGTT). The glucose goes to the beta cells in the pancreas where it attaches to glucose receptors, signalling the beta cells to release insulin. The released insulin travels by the bloodstream to the peripheral tissues where both muscle and fat cells have insulin receptors. The insulin attaches to such receptors and thereby facilitates entry of glucose into the cells.

Data collected on patients with reactive hypoglycemia indicates that their glucose and/or insulin receptors are defective. When the glucose receptor on the beta cell is defective, insulin release is poor and/or delayed. When the insulin receptor is defective the glucose cannot enter the cell and the blood level rises and continues to rise. Because the cells are not getting glucose, a message goes back to the pancreas to secrete more insulin. Insulin production is stimulated from the beta cell giving a delayed insulin peak. Suddenly, the higher insulin levels are able to get the glucose into the cell, the blood glucose plummets and the symptoms of hypoglycemia are apparent.

The results of OGTT on patients exhibiting symptoms of reactive hypoglycemia reveal that, among the prepubertal and younger postpubertal, glucose tolerance is not grossly abnormal but insulin levels are inappropriately high. In the older postpubertal subjects, both glucose and insulin responses are abnormal. Patients between 25 and 45 are all normal weight, have glucose responses characterized by high insulin levels early and symptomatic hypoglycemia at 3½ to 4 hours. Adults older than 45 are all overweight or obese and have very high glucose and insulin levels. They are divided into two groups; one has a delayed first peak insulin, the other has two markedly elevated peaks of insulin. All subjects had symptoms of hypoglycemia occurring between 2½ to 3½ hours in the first OGTT. Symptoms of hypoglycemia are very similar among the subjects; younger children are hyperactive and disruptive in school; older children are doing poorly in their studies, as are the young adults; older adults are depressed and very irritable near mealtime.

According to the present invention, oral diazoxide, taken at doses that are considerably lower than the recommended dosages for treatment of hyperinsulinism, can be used successfully to stabilize glucose utilization in such patients and relieve or reduce the associated symptoms such as malaise, depression and lack of concentration.

The effect of the tiny doses of diazoxide is to normalize the position and level of the glucose and insulin peaks. Although not intended to be limiting, this suggests that the drug is enhancing the ability of both the glucose and the insulin receptors to act normally. The diazoxide is not curative and it must be taken with each meal because its half life is only 2½ to 3 hours; its effectiveness is generally gone by 5 hours.

A preferred dosage used is in the range of 0.4 to 0.8 mg/kg of ideal body weight, taken 10 to 15 minutes before each meal. The dosages may vary with mealtime depending on the caloric intake. Dosages are all individualized by the physician. The hypoglycemic symptoms of some adults are better controlled if they split total calories of each meal and the mealtime diazoxide dose with a snack taken between meals and bedtime.

A preferred protocol for testing the effectiveness of diazoxide involves a regular OGTT followed within a week with an OGTT preceded 15 minutes by a dose of diazoxide of 0.4 mg/kg ideal body weight. Plasma glucose and insulin levels are determined at −15, 0, 15, 30 minutes and every half hour thereafter through 4 hours. Alternatively, an initial OGTT may be followed by a second OGTT after 4 to 6 months of diazoxide therapy.

The normalization of glucose and insulin levels in the majority of patients, even after only one dose, is striking. The lowering of both glucose and insulin levels strongly suggests that the diazoxide is enhancing activity of the glucose receptor on the beta cell and the insulin receptor on the peripheral muscle cell. With prompt secretion of insulin and normalization of peripheral glucose utilization in the muscle cell, further stimulation of insulin is unnecessary.

A majority of affected subjects over 50 years of age are overweight and a group of younger women, studied in their 30's and 40's after by-pass surgery or stapling, had become morbidly obese in their teens (Example 6). The insulin receptor in the fat cell, in contrast to the insulin receptor in the muscle cell, is normal. The data suggest that over time, the increased glucose entry into the fat cell stimulates an increase in body fat and subjects become overweight or obese. Thus, the data suggest that obesity develops as a result of insulin resistance, rather than, as is currently postulated in the literature, the obesity causing the insulin resistance. These data further support the hypothesis that the subjects with hyperglycemia/hypoglycemia/hyperinsulinism under study who respond to diazoxide are early Type II diabetic subjects. It also suggests the possibility that normalization of defective glucose metabolism through treatment with diazoxide may be useful in the treatment of obesity.

In addition to relieving the symptoms of hypoglycemia, it is also believed that the use of diazoxide may provide long range benefits by preventing the onset of insulin dependency in Type II diabetic subjects. It is quite possible that continued stimulation of the beta cell by the high glucose levels results in increased insulin content of each cell (hypertrophy) and increased numbers of beta cells (hyperplasia). Over time, many persons with Type II diabetes lose their insulin producing capacity and must take injections of insulin. This continued hyperstimulation of the pancreas could eventually exhaust the beta cells and account for the need for exogenous insulin. By enhancing glucose receptor and insulin receptor activity and thereby normalizing blood levels of both glucose and insulin, not only are the symptoms of hypoglycemia relieved, but the removal of the persistent stimulation of the beta cells may prevent their deterioration.

86 people were tested who had been characterized as having hyperinsulinism. Those reliably taking the medicine were all benefited.

The subjects fell into several categories. Out of the 85, 15 pairs were a child and his or her mother or father. Two of the sets involved a child, a mother and a grandparent, clearly indicating operation of a genetic factor. There also appeared to be a pattern where a family member was a Type I or insulin dependent diabetic subject. Seven subjects had a relative in the nuclear family with insulin dependent diabetes. An oral glucose tolerance test was used to detect the abnormalities in these subjects. In the normal oral glucose tolerance test the insulin peak occurs at 30 minutes and then falls, and there is a small peak at $2\frac{1}{2}$ hours, and by the 4th hour the insulin level is back to the fasting level. The glucose peaks at 30 minutes, then declines, followed by a small peak at $2\frac{1}{2}$ hours and a return to fasting levels by 4 hours. All subjects had normal fasting levels of both glucose and insulin.

Several abnormalities in glucose metabolism were found to be treatable with oral diazoxide. These abnormalities were observed in all subjects in response to the oral administration of glucose. The abnormalities could be characterized according to four distinct patterns. The first group had an absent first insulin peak and a high, delayed insulin peak around 90 minutes. The glucose peak was also delayed with a high peak at 60–90 minutes and then marked hypoglycemia at 3–$3\frac{1}{2}$ hours. The second group had an initial insulin peak that continued to rise and which ended in a very late peak at 90 minutes followed by a small second peak at $2\frac{1}{2}$ hours. The glucose rose with a peak at 90 minutes and then a marked drop to hypoglycemic levels at 3 and $3\frac{1}{2}$ hours. The third group had early hyperinsulinism with a very high peak at 30 minutes, a second very high peak at 90 minutes and a third peak around 3 hours. The glucose peaked at 30 minutes with a sudden drop, a rise and then a drop again. At both drops in glucose the patients exhibited severe hypoglycemic symptoms. The fourth group, a group of young children, exhibited a very poor insulin response with initially high glucose which fell precipitously.

Treatment of all of the above groups with diazoxide brought insulin peaks to normal position and intensity, with a tremendous relief of symptoms even after only one dose.

A large number of patients were discovered to have an abnormal glucose tolerance test and a positive response to diazoxide. The results suggest that individuals diagnosed with symptoms in the following categories should be tested: (1) hyperactive children—3 subjects were placed on Ritalin without benefit; (2) children, adolescents, or young adults with failing grades, inattentiveness or even sleeping in class; (3) patients with syncope and increased heart rate—one 17 year old was considered for a pacemaker; (4) depressed patients of any age; (5) morbidly obese subjects before being subjected to by-pass surgery or stapling; and (6) unexplained loss of consciousness with or without seizure disorders in children and adolescents.

The following examples serve to illustrate the method of the invention without restricting said process.

EXAMPLE 1

A ten year old boy had hypoglycemia. This boy's hypoglycemia was accompanied by hyperinsulinism. His mother's history and glucose tolerance testing indicated that she had been a gestational diabetic. On the basis of these studies, it appeared that the boy's hyperinsulinemia was due to either being an offspring of a diabetic woman or of being pre-diabetic. The boy was placed on high protein frequent feeding and asked to return in two years for retesting or sooner if symptoms of diabetes developed. In two years he was retested because nothing unusual had happened during the interval, and at this time his insulin levels were even higher but his blood glucose at 2 and 3 hours were high (145 milligrams %). The mother was shown how to do blood glucose tolerance testing. Shortly thereafter, he became showered with nevi and like his mother had the dysplastic nevi syndrome which carries the risk of malignant degeneration. Since insulin is a growth stimulant and could possibly stimulate the growth or numbers of nevi, diazoxide was administered to reduce the insulin levels. A very small dose of diazoxide, 3 milligrams per kilo per day, prior to each meal, was administered. Within two days the boy's two hour post meal sugar was 80 milligrams % instead of the 145. His hypoglycemic symptoms were gone and seven weeks later in an oral glucose tolerance test he showed marked improvement of glucose and insulin levels.

EXAMPLE 2

Mrs. D. T. was experiencing acute periods of depression and had night-sweats. She had early morning wakings, bad dreams, and was on heavy doses of psychotropic medication. She had been on increasing amounts of thorazine for many years prescribed by her psychiatrist of thirteen years. Prior to the oral glucose tolerance test she was taking 300 mg of thorazine, 6 mg of ortane, 400 mg of Tegretol and 30 mg of novane daily. One week after starting diazoxide she was able to stop taking thorazine and after 4 months she has been able to eliminate the ortane. She has no periods of depression or drowsiness after meals and her level of energy has increased.

EXAMPLE 3

Mr. D. T. had severe drowsy spells and great seizures of anger followed by some feelings of despair. His glucose levels after eating sweets measured below 40 on the glucometer. As long as he takes oral diazoxide prior to meals, these feelings have mostly subsided and his blood sugar (as measured by a glucometer) is no longer low.

EXAMPLE 4

A. C. was in law school which demanded concentration and long hours. About two to three hours after eating, she would be overcome by an uncontrollable sleepiness, faintness and crabiness. She always had periods in her life when she could not get out of bed, not due to mental depression, but rather due to physical depression of her motor movements and energy.

Upon beginning treatment with oral diazoxide, she no longer requires naps in the afternoon. She wakes up earlier and earlier every day and her productivity has increased greatly.

EXAMPLE 5

J. L. spent many years coping without energy and became increasingly depressed. Her energy level came in bursts-particularly after eating refined sugars-followed by very deep valleys of non-production. The use of oral diazoxide taken before meals has eliminated all the previous fluctuations in her energy levels. Her depression has decreased and she now looks forward to planning future events. An added benefit of the medication is a gradual weight loss.

EXAMPLE 6

A group of morbidly obese women who upon having the stapling or bypass procedure to help them reduce weight became markedly symptomatic with hypoglycemia when they reached levels of weight around 160-170 having lost from 300-400 lbs. Testing of six of these individuals showed that they were hyperglycemic, hypoglycemic and hyperinsulinemic. Treatment with oral diazoxide was very effective in such patients, suggesting they are Type II diabetics or a variant thereof. One woman had her stomach stapled for obesity (250 pounds) in September, 1989. In February, 1990, when she reached 175 pounds, she began to experience symptoms relieved by eating foods with a great deal of added sugar. Another woman was referred because of similar symptoms supervening when on a self-imposed diet she went from 230 pounds to 160 pounds. Both of these women who had developed hypoglycemia had markedly abnormal insulin response to oral glucose and both were markedly relieved by oral diazoxide.

EXAMPLE 7

Figure 1B:
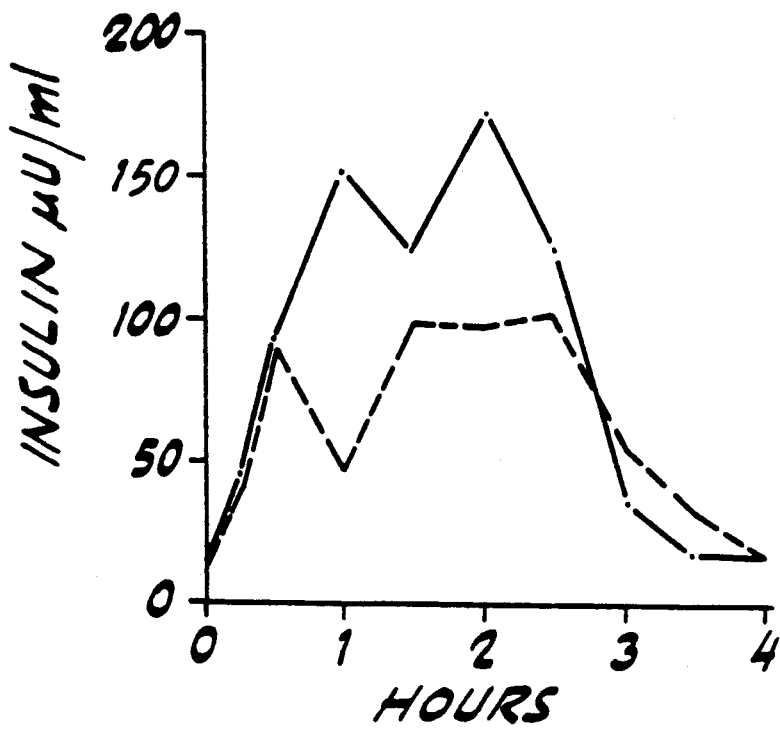

FIG. 1A and 1B demonstrate the effect of a single dose of oral diazoxide in a grandmother having defective glucose metabolism. Normal glucose utilization is shown in FIG. 1A by a solid line. The (- - -) lines in FIGS. 1A and 1B indicate utilization of glucose by the patients in the absence of diazoxide. The (.--.--.) line indicates the effect of 0.4 mg/kg oral diazoxide taken 15 minutes before the glucose tolerance test. Reduction of both glucose and insulin to normal levels was observed.

EXAMPLE 8

Figure 2A:
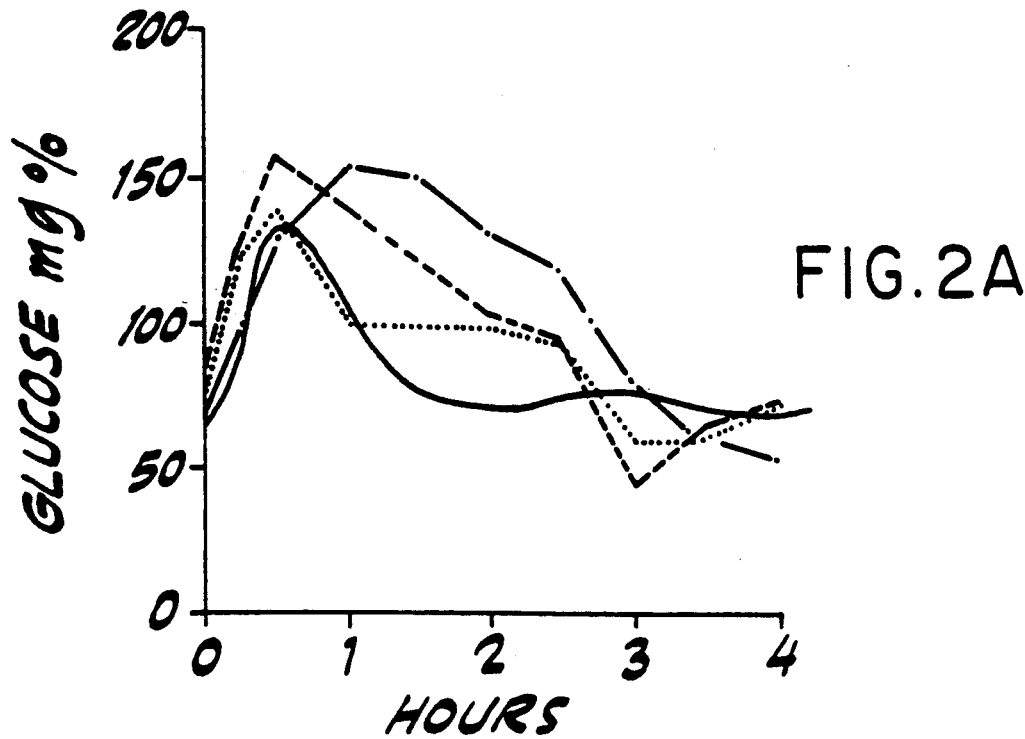
FIG. 2A and 2B demonstrate defective glucose metabolism in three generations of a family.
Figure 2B:
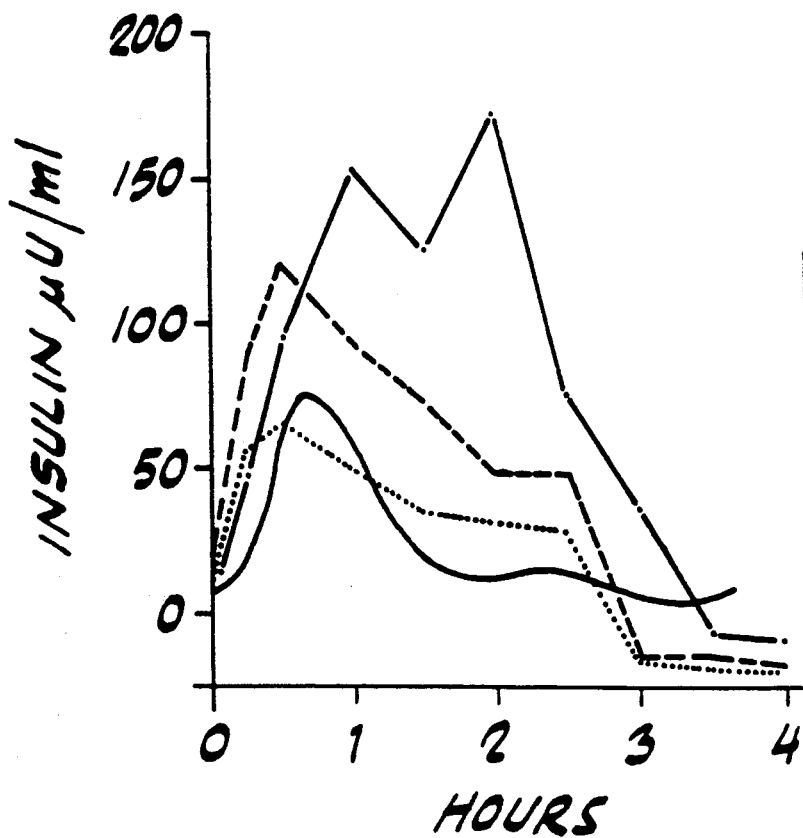

Glucose utilization and insulin production were measured in 3 generations of a family (FIG. 2). The 13 year old, male child, is normal weight, as is his 34 year old mother. Her 58 year old mother is obese. Normal glucose tolerance and insulin production after ingestion of glucose in a standard glucose tolerance test is shown by the solid lines in FIGS. 2A and 2B. The 13 year old's glucose tolerance (. . . ; FIG. 2A) shows a partial utilization of glucose which eventually plateaus out, followed by hypoglycmia. His mother (- - -) utilized glucose much more slowly, but experienced similar hypoglycemia. The grandmother's glucose tolerance curve (.--.--.) was shifted to the right, indicating poor response of the pancreas caused by continuous overproduction of insulin.

EXAMPLE 9

Figure 3A:
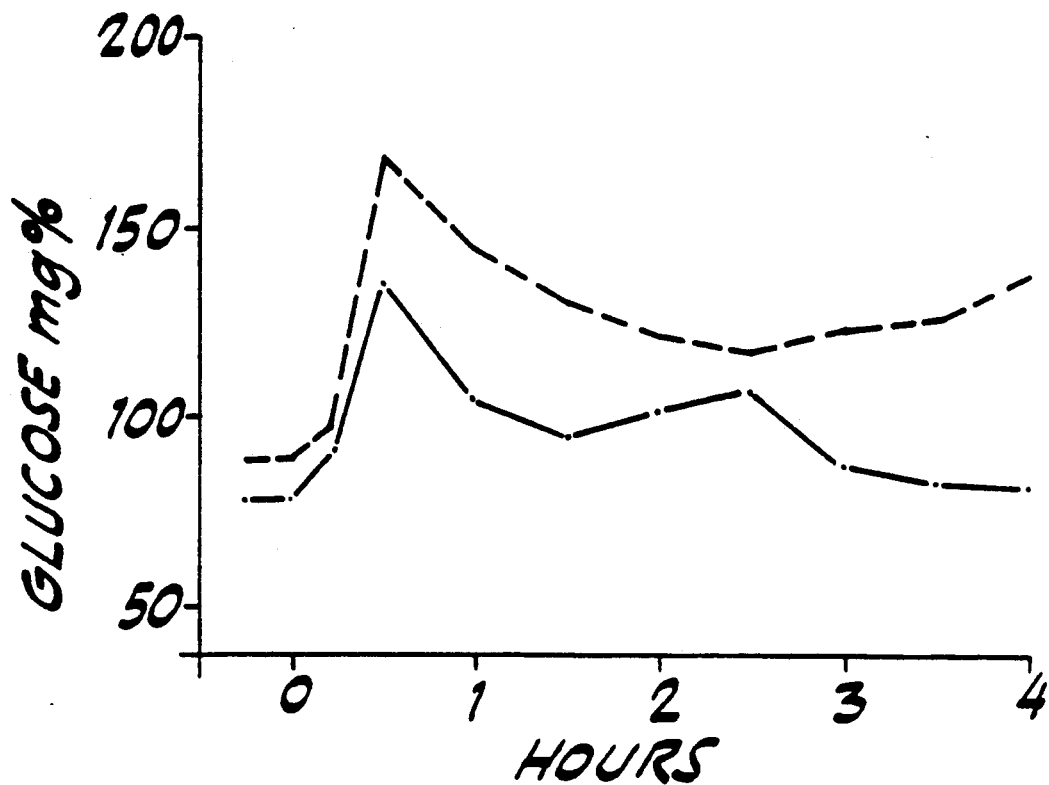
FIG. 3 demonstrates glucose utilization and insulin production before and after five months of treatment with diazoxide.
Figure 3B:
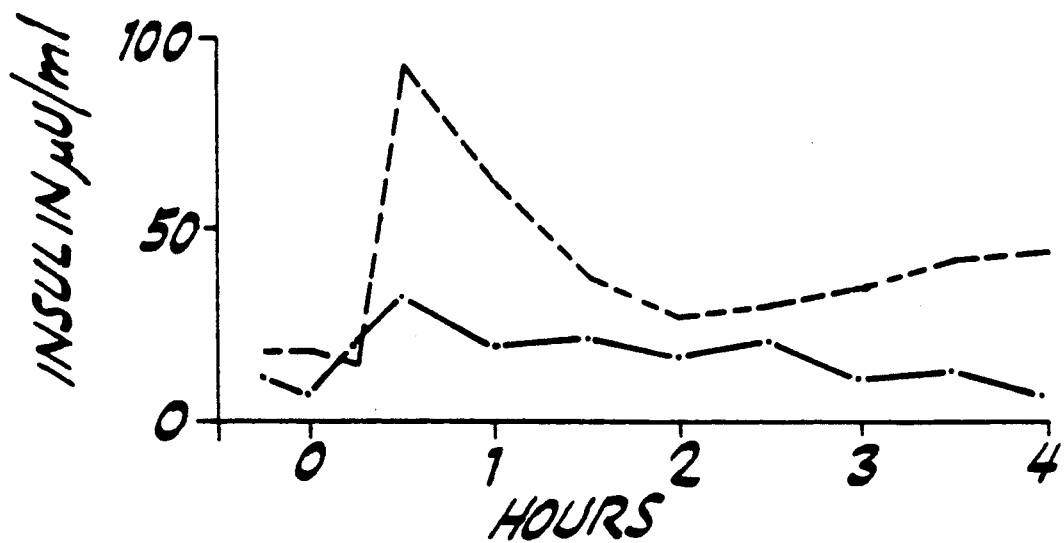

Glucose utilization and insulin production were measured before treatment (- - -) and after 5 months treatments with diazoxide (.--.--.) in a 14 year old hyperinsulinemic male (FIG. 3). Insulin production and glucose utilization were significantly normalized after treatment.

EXAMPLE 10

Figure 4A:
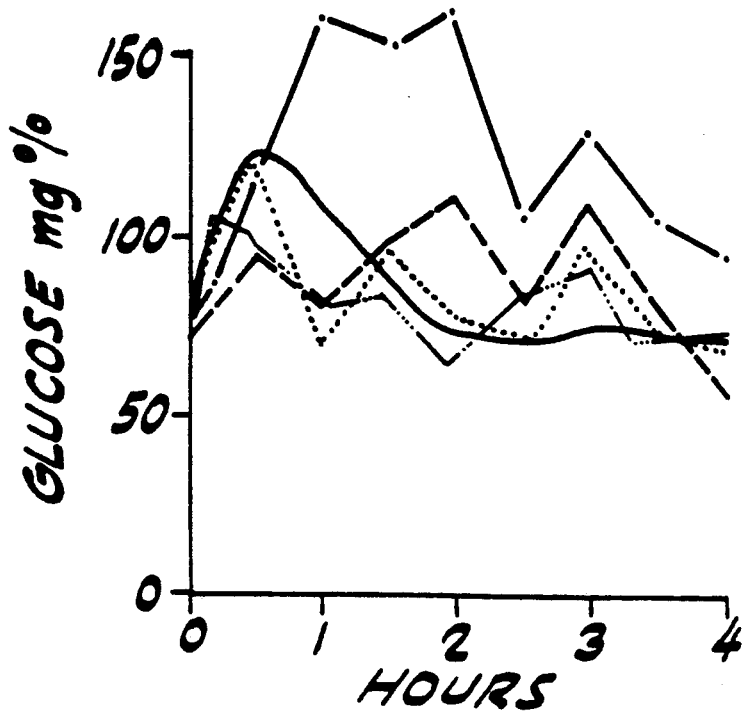
FIG. 4 depicts the results of glucose tolerance tests after 1 dose, 9 months and 11 months on diazoxide.
Figure 4B:
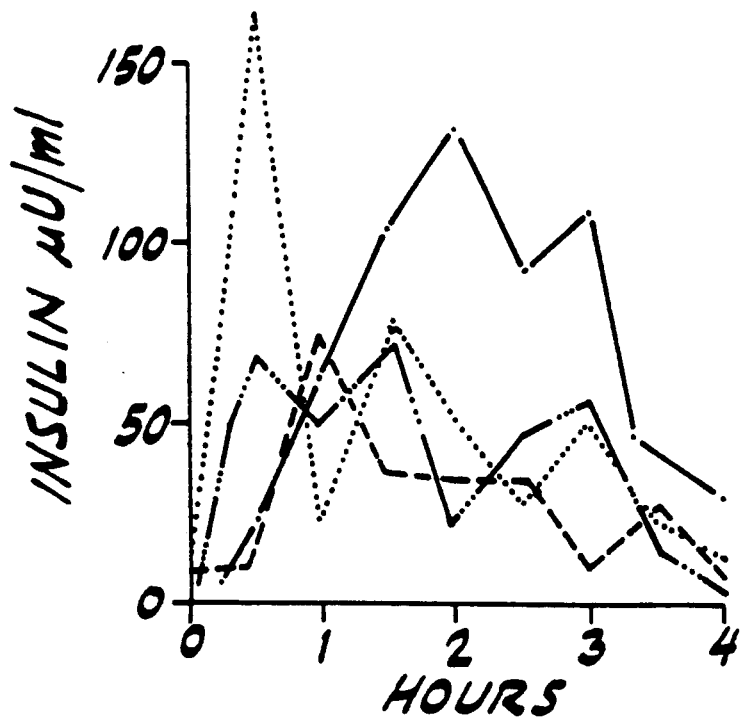

A glucose tolerance test was run on a 20 year old male subject with a delayed (2 hour) insulin peak (.--.--.). Similar tests were run after a single dose (- - -), 9 months (. . . ) and 17 months (--..--..--). Treatment with only one dose of diazoxide shifted the insulin peak to the first hour. A significant trend to normal glucose and insulin levels was observed after 9 and 17 months. Normal glucose utilization is indicated by a solid line in FIG. 4A.

EXAMPLE 11

Figure 5A:
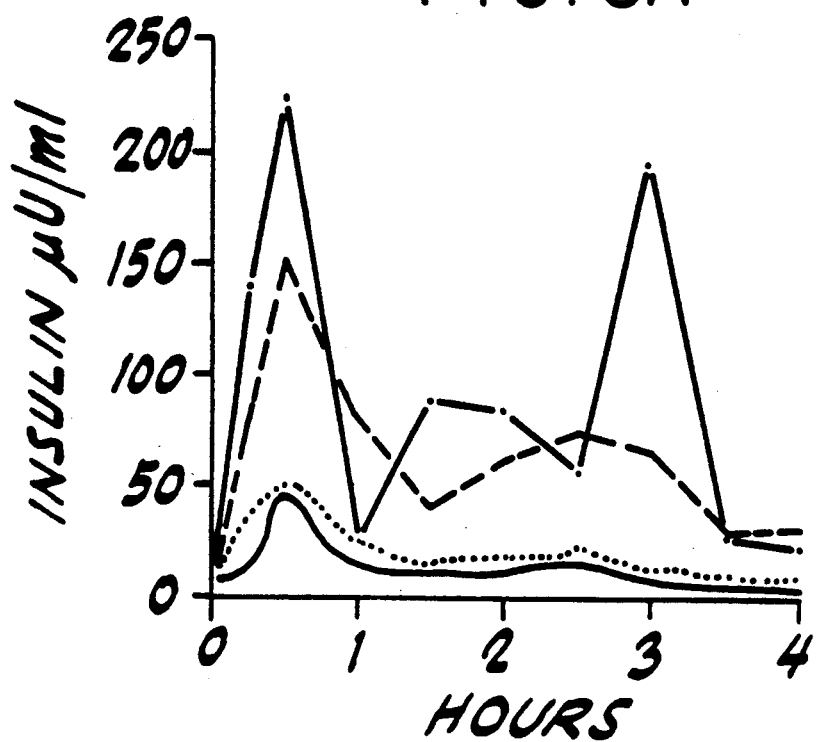
FIG. 5 depicts the results of a glucose tolerance test before and after oral diazoxide.
Figure 5B:
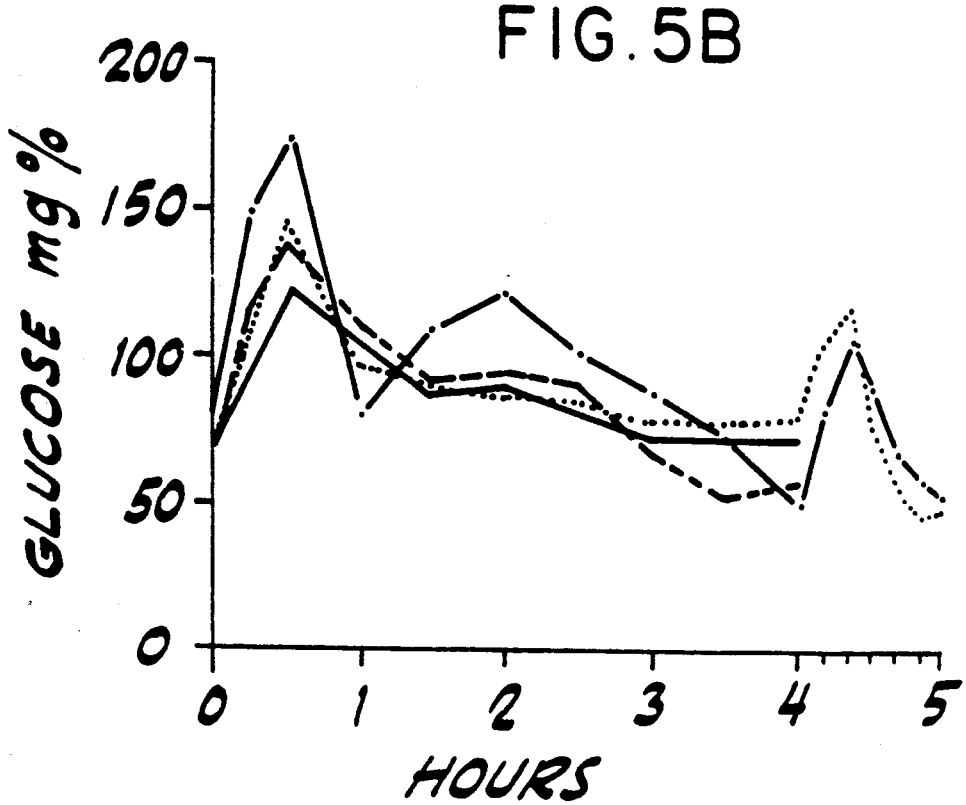

FIGS. 5A and B depict the results of a glucose tolerance test in a 14 year old male before and after oral diazoxide treatment. Prior to treatment (.--.--.), the patient exhibited a second insulin peak and concomitant hypoglycemic symptoms. After only one dose of diazoxide (- - -), the second insulin peak was eliminated. After 6 months of oral diazoxide (. . . ), the patient's glucose tolerance was relatively normal. Normal glucose utilization is by a solid line in FIG. 5A.

I claim:

1. A method for normalizing blood glucose and insulin levels as measured by an oral glucose tolerance test in an individual exhibiting normal fasting blood glucose and insulin levels and exhibiting in an oral glucose tolerance test elevated glucose levels and at least one insulin level abnormality selected from the group consisting of a delayed insulin peak, an exaggerated insulin peak and a secondary elevated insulin peak, said method comprising administering diazoxide to said individual before ingestion of a food source in an amount effective to normalize said blood glucose and insulin levels, wherein said diazoxide is administered in an amount from about 0.4 to about 0.8 mg/kg body weight before each meal.

2. A method according to claim 1 wherein said insulin level abnormality in a secondary elevated insulin peak, and wherein said individual exhibits in an oral glucose tolerance test three insulin peaks at about 30 minutes, about 90 minutes and about 3 hours and two elevated glucose peaks at about 30 to about 60 minutes and at about 2 hours to about 2.5 hours.

3. A method according to claim 1 wherein said insulin level abnormality is a delayed insulin peak, and wherein said individual exhibits in an oral glucose tolerance test a poor first insulin peak followed by said delayed insulin peak at about 90 minutes and an elevated glucose peak at about 60 to about 90 minutes after said delayed insulin peak.

4. A method according to claim 1 wherein said insulin level abnormality is a secondary elevated insulin peak, and wherein said individual exhibits in an oral glucose tolerance test an initial insulin peak followed by a second peak at about 90 minutes and a third peak at about 2.5 hours and hypoglycemia at about 3 hours to about 3.5 hours.

5. A method according to claim 1 wherein said diazoxide is administered orally.

6. A method according to claim 1 wherein said administration of diazoxide causes the magnitude of said blood insulin and glucose levels to approximate more closely the normal pattern.

7. A method according to claim 1 wherein said administration of diazoxide causes the timing of peaks in said blood insulin and glucose levels to approximate more closely the normal patterns.

8. A method according to claim 1 wherein said diazoxide is administered within 30 minutes before a meal.

9. A method according to claim 8 wherein said diazoxide is administered about 10 to about 15 minutes before a meal.

* * * * *